United States Patent

Brommersma

[11] Patent Number: 5,351,691
[45] Date of Patent: Oct. 4, 1994

[54] ENDOSCOPIC PROBE

[75] Inventor: Pieter D. Brommersma, Hamburg, Fed. Rep. of Germany

[73] Assignee: B.V. Optische Inductrie "De Oude Delft", Delft, Netherlands

[21] Appl. No.: 969,211

[22] PCT Filed: Jul. 31, 1991

[86] PCT No.: PCT/NL91/00141
§ 371 Date: Feb. 22, 1993
§ 102(e) Date: Feb. 22, 1993

[87] PCT Pub. No.: WO92/02178
PCT Pub. Date: Feb. 20, 1992

[30] Foreign Application Priority Data

Aug. 2, 1990 [NL] Netherlands .................. 9001755

[51] Int. Cl.$^5$ .................................................. A61B 8/12
[52] U.S. Cl. .................................. 128/662.06; 128/4; 128/662.03
[58] Field of Search ................. 128/660.09, 660.10, 128/660.08, 661.01, 662.06, 661.04, 4, 662.03

[56] References Cited

U.S. PATENT DOCUMENTS 4,543,960 10/1985 Harui et al. .................. 128/662.06
4,787,247 11/1988 Wuchinich et al. ............ 128/660.10
4,834,102 5/1989 Schwarzchild et al. ....... 128/662.06

Primary Examiner—William E. Kamm
Assistant Examiner—George Manuel
Attorney, Agent, or Firm—Louis E. Marn

[57] ABSTRACT

An endoscopic probe suitable for use as a TEE-probe, comprising a flexible tube having at one end a probe head which is provided with a phased array type ultrasonic transducer comprising a number of elongated transducer elements which elements can be individually electrically controlled by means of cables connected to the individual elements and extending through the flexible tube. The transducer is fitted in an essentially cylindrical transducer housing which is mounted in the probe head with its longitudinal axis extending perpendicularly to the longitudinal axis of the probe head. The transducer housing is fitted rotatable in the probe head in such a way that the transducer is rotatable in the plane of the array by a driver cooperating with the transducer housing. By means of at least on flexible printed circuit board the elongated transducer elements are connected to cables extending through the flexible tube. The at least one flexible printed circuit board extends through an opening into the transducer housing, is present in the transducer housing in a loop shape and ends at least at a number of connecting electrodes of transducer elements.

12 Claims, 3 Drawing Sheets

ENDOSCOPIC PROBE

BACKGROUND OF THE INVENTION (1) Field of the Invention

The invention relates to an endoscopic probe, in particular suitable for use as a TEE probe.

(2) Brief Desciption of the Prior Art

An endoscopic probe is known from the article "An endoscopic micromanipulator for multiplanar transesophageal imaging" by Roy W. Martin et al. in Ultrasound in Med & Biol., Vol. 12, No. 12, pp. 965–975, 1986. The known device has a probe head with a slightly flattened part containing an essentially flat transducer made up of a number of individual adjacent elongated elements of piezoelectric material which can be excited individually, and which together form a phased array. By exciting the strip-type elements in a suitable sequence, it is possible to obtain a beam which scans the environment to be examined and produces reflections in a plane lying at right angles to the elongated elements, as described in greater detail by J. C. Somer in "Echocardiography", N. Bom, published by Martinus Nijhof in The Hague, 1977. Rotating the flexible tube, and thus the probe head, about the longitudinal axis means that the environment around the probe head can be scanned by an ultrasonic beam. Pulling cables also extend through the flexible tube, by means of which said head can be pulled forwards or backwards.

In the medical world there is a need for an endoscopic probe with which more information can be obtained. In the past is was proposed that a biplane TEE probe should be used for this purpose. Such a probe head has two transducer arrays lying one after the other In the lengthwise direction of the flexible tube and the head, and again composed of adjacent elongated elements. The elements of one transducer extend at right angles relative to the elements of the other transducer. With this head it is therefore possible to obtain two scanning beans which can carry out a scanning movement in directions extending at right angles to each other.

A disadvantage of this known probe is that the scanning beams originate in two different points. Another disadvantage is that the rigid head is relatively long, which can lead to problems in practical use. Two separate transducer arrays with the same definition per array also require twice the number of control cables, which all have to be conveyed through the flexible tube. However, the flexible tube has little or no space for these. In order to overcome these disadvantages the U.S. Pat. No. 4,543,960 proposes to mount the transducer array in the probe head rotatable about an axis extending perpendicularly with respect to the plane of the array. For that purpose a transducer housing carrying the transducer array has been mounted in a cavity in the probe head, which housing is rotatable about a top provided at the side of the transducer housing facing away from the array. Via conductors formed on two flexible printed circuit boards the elements of the transducer array are connected to the conductors of one or more electrical cables extending through the flexible tube. The flexible printed circuit boards are present in a spiral shape around the transducer housing.

SUMMARY OF THE INVENTION

The object of the invention is to eliminate the outlined disadvantage, and more generally to provide a reliably working endoscopic probe of small dimensions by means of which the human body can be echographically examined internally in the optimum manner. For this, according to the invention a device of the above-described type is characterized in that the at least one flexible printed circuit board extends through an opening in the transducer housing, is present in the transducer housing in a loop shape and ends at at least a number of connecting electrodes of transducer elements.

The invention will be described in greater detail b-low with reference to the appended drawing of a number of examplary of embodiments.

BRIEF DESCRIPTION OF THE DRAWINGS

FIGS. 1 to 3 show a TEE probe as an examplary embodiment of the invention. A TEE (trans esophageal echocardiography) probe is a device which can be used to examine the heart, or other parts of the body in the region of the esophagus, by ultrasonic radiation from the oesophagus through the oesophagus wall. The device shown comprises a probe head 1 with a housing 2, which connects to a flexible end part 3 of a flexible tube which is not shown. Using Bowden cables 4, 5 extending through the flexible tube, the probe head can be bent forwards (as shown in FIG. 2) or backwards. This movement is made possible by the end part 3. If desired, similar Bowden cables which permit a sideways swing of the probe head can be present.

Figure 1:
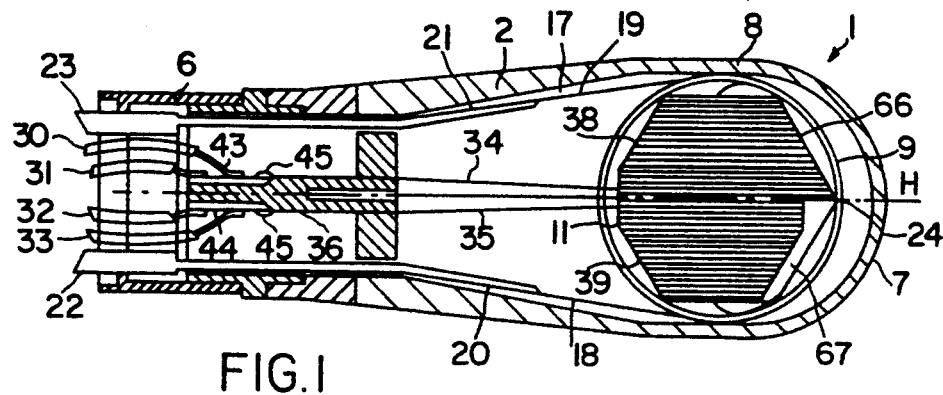
FIG. 1 shows schematically a cut-away top view of an example of an embodiment of a probe head of a TEE Probe head according to the invention.

The housing 2 connects by means of a connecting piece 6 with round cross-section to the end part 3 of the flexible tube, but has itself an essentially rectangular cross-section with rounded edges which widens out slightly to a holder 8 which is shut off at the free end by a semi-circular wall 7, and in which an ultrasonic transducer of the phased array type is placed. The holder 8 is provided with a circular aperture 9 in an essentially flat top wall. Situated in and behind the aperture is the transducer which, as can be seen in FIG. 2, comprises an essentially flat transducer 11 lying on a backing layer 10. The transducer 11 is made up of a number of adjacent, but separate strip-type transducer elements which can be, for example, piezoelectric elements, and which in the situation shown in FIG. 1 extend parallel to the longitudinal axis H of the probe head. The backing layer absorbs ultrasonic vibrations which are radiated towards the interior of the probe head and which, if not absorbed, would lead to disturbing reflections. The backing layer 10 is confined inside an electrically insulating frame 12 which can be made of, for example, a suitable plastic.

Above the array 11 an acoustic lens 13 is present. In a suitable manner phasedly exciting the individual strip-type transducer elements makes it possible to obtain an ultrasonic beam which can scan an area the shape of a sector of a circle in a plane at right angles to the strip-type elements. This technique, which is known per se, can therefore be used to scan the environment of the probe head with a swinging beam, but the swing can take place in only one plane.

The lens 13, the transducer 11, the frame 12 and the backing layer 10 are placed in a transducer housing 14 which is an essentially cylindrical shape. The transducer housing 14 sealed at the level of the aperture 9 by the lens 13, and in the example shown also has a bottom 15 which is supported on a pin 16 fitted in a bore in the wall of the housing of the probe head opposite the aperture 9. The central axis of the pin coincides with the central axis H2 of the transducer housing, and the centre point of the circular aperture lies on said central axis H2, so that the transducer housing is rotatable about the pin.

Figure 2:
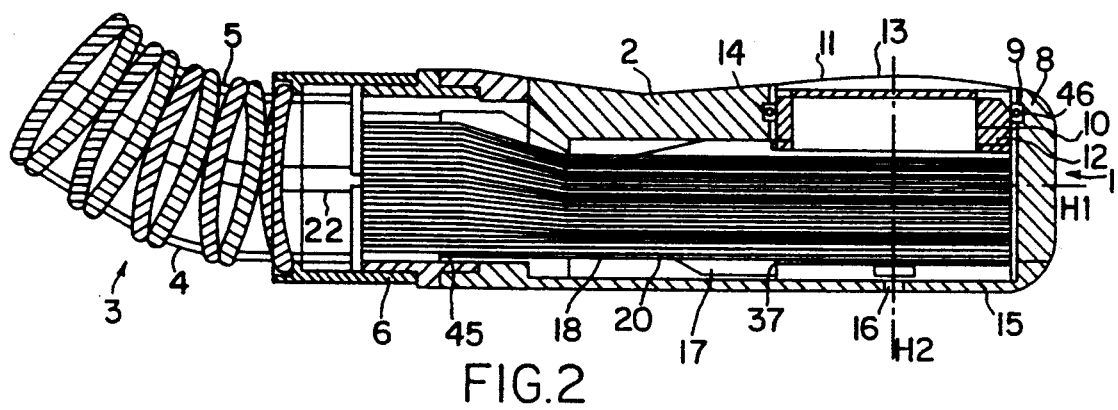
FIG. 2 shows schematically a cut-away side view of the probe of FIG. 1.
Figure 3:
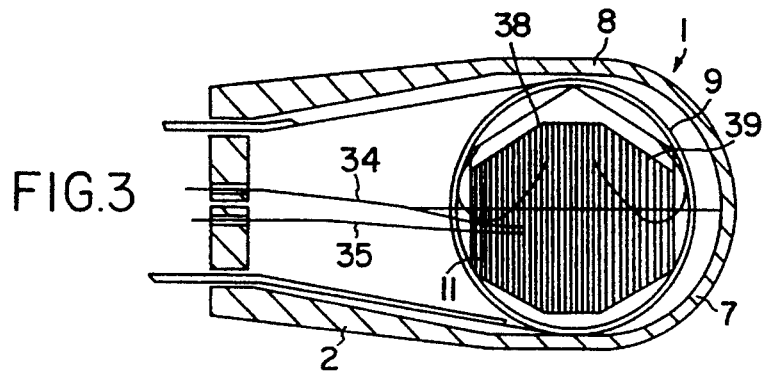
FIG. 3 shows schematically a top view of the probe head of FIG. 1, in a different working position.

In the examplary embodiment shown, the transducer housing is rotatable from the rest position shown in FIG. 1 both clockwise and anticlockwise through approximately 90 degrees. FIG. 3 shows the probe head with a transducer 11 rotated through 30 degrees. The total rotation range is therefore 180 degrees, which means that a spatial area the shape of the sector of a sphere can be scanned completely with one and the same disc-type transducer made up of strips, without changing the position of the probe head itself.

In order to make the transducer housing 14 rotate, in this exemplary embodiment a belt 17 is placed around the transducer housing, the two free ends 18, 19 of which belt are connected to pulling cables 20, 21. The pulling cables are again in the form of Bowden cables, the outer cables of which are shown at 22, 23. The belt 17 can be a spring steel belt which is connected by a single spot weld to an interposed metal strip which is in turn fixed to the plastic transducer housing 14. The SpOt weld in the rest position is on or near the longitudinal axis H1 of the probe head, as shown at 24 in FIG. 1.

Figure 4:
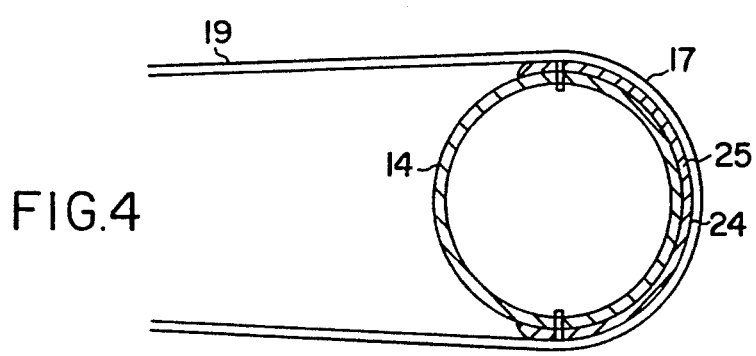
FIG. 4 shows a detail of the probe of FIGS. 1 and 2.

All this is shown again in FIG. 4. The interposed metal strip is indicated by 25 and is connected in a suitable manner to the transducer housing. This prevents the pulling belt from slipping over the transducer housing.

For the electrical connection between the transducer elements and the electrical cables passed through the flexible tube, use is made of a flexible printed circuit board on which conductor tracks, connected at one side to the individual transducer elements and at the other side to the cores of the electric cables, are provided.

A number of cables are indicated by 30 to 33 in FIG. 1. The flexible printed circuit board is indicated by 34, 35. The flexible printed circuit board extends from a supporting plate 36 situated in the part of the probe head 1 connecting to the flexible tube and reaches into the transducer housing 14. For this purpose, the transducer housing is provided with a recess 37 extending through approximately 180 degrees along the periphery and being the height of the width of the flexible printed circuit board. Under the backing layer the transducer housing 14 contains two pins 38, 39 which are fixed on the bottom 15 and/or in the backing layer 10. A strip of the flexible printed circuit board is passed around each of the pins 38, 39. Each strip extends under the backing layer in a loop towards connecting electrodes fitted on one end of the striptype transducer elements. The flexible printed circuit boards thus do not take up any space around the transducer housing.

In the examplary embodiment shown, the connecting electrodes for all strip-type elements are on the front side of the probe head. It is, however, also possible, for example, to fit the electrodes for the even-numbered elements on the front side and the electrodes for the odd-numbered elements on the opposite side of the transducer. Preferably the pins 38, 39 have been placed such that the flexible printed circuit boards extend substantially through the rotation axis H2 of the transducer housing not only in the rest position shown in FIG. 1 but also on rotation of the transducer housing. Thereby rotation of the transducer housing 9 does not lead to a change of the space needed for the flexible printed circuit boards. The parts of the flexible printed circuit boards extending outside the transducer housing change position only to a very small degree during rotation of the transducer housing, as a comparison of FIGS. 1 and 3 may show. The pins 38, 39 as shown can be placed each on a side of the axis H just past the centerline extending perpendicularly to the axis.

The supporting plate 36 in this example bears on both sides printed circuit boards 43, 44 with conductor tracks to which the ends of the cables 30 to 33 are connected. The connecting point between the conductors of the printed circuit boards 43, 44 and the conductors of the flexible printed circuit board is indicated at 45.

Figure 5:
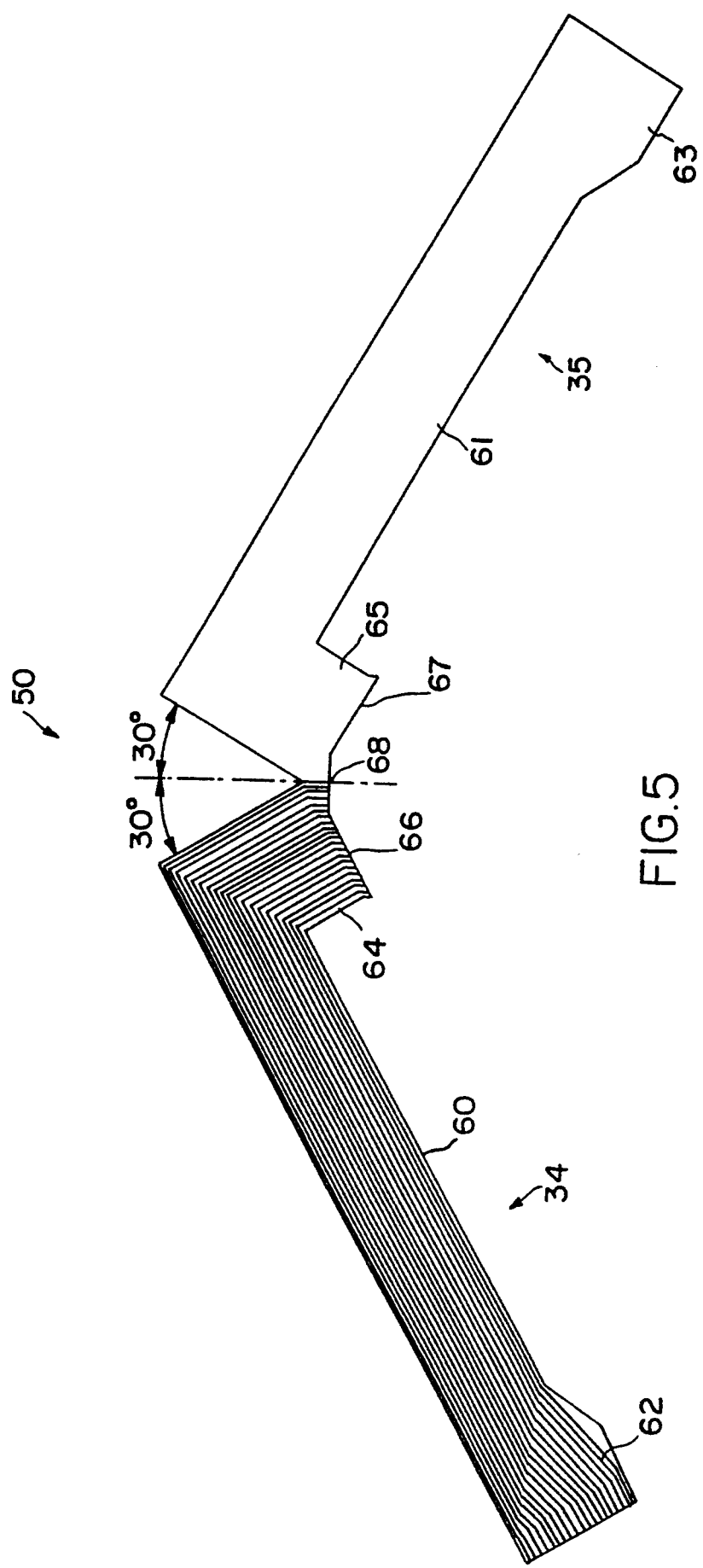
FIG. 5 shown an example of a special printed circuit board which can be used in a probe according to the invention.

FIG. 5 shows schematically a flat blank of a flexible printed circuit board 50 which can be used in the device described. The printed circuit board shown has two wing strips 34, 35 which together form an approximately V-shaped flat blank. Each wing 34, 35 has an elongated part 60, 61 which has a first end 62, 63 for connection to the printed circuit boards 43, 44. Each wing also has a short transverse part 64, 65 which in the fitted state rests against the transducer housing 14 at the front side (in FIGS. 1 or 2). The transverse parts each have an end strip 66, 67. The end strips of the two transverse parts are connected to each other at 68 and thus form the connection between two wing strips. The end strips in the fitted state are folded over approximately at right angles and at the bottom side lie against the connecting electrodes of the transducer elements. The connecting electrodes can be, for example, gold electrodes, and the connection can be made with conducting adhesive.

It is being noted that the width of the elongated parts of the wing strips of the described flexible printed circuit boards together with the thickness necessary for the backing layer to a large degree determine the minimal height of the probe head. According to a further embodiment of the idea behind the invention the elongated parts 60, 61 in their mounted state have been folded about a folding line extending in the longitudinal direction.

Figure 6:
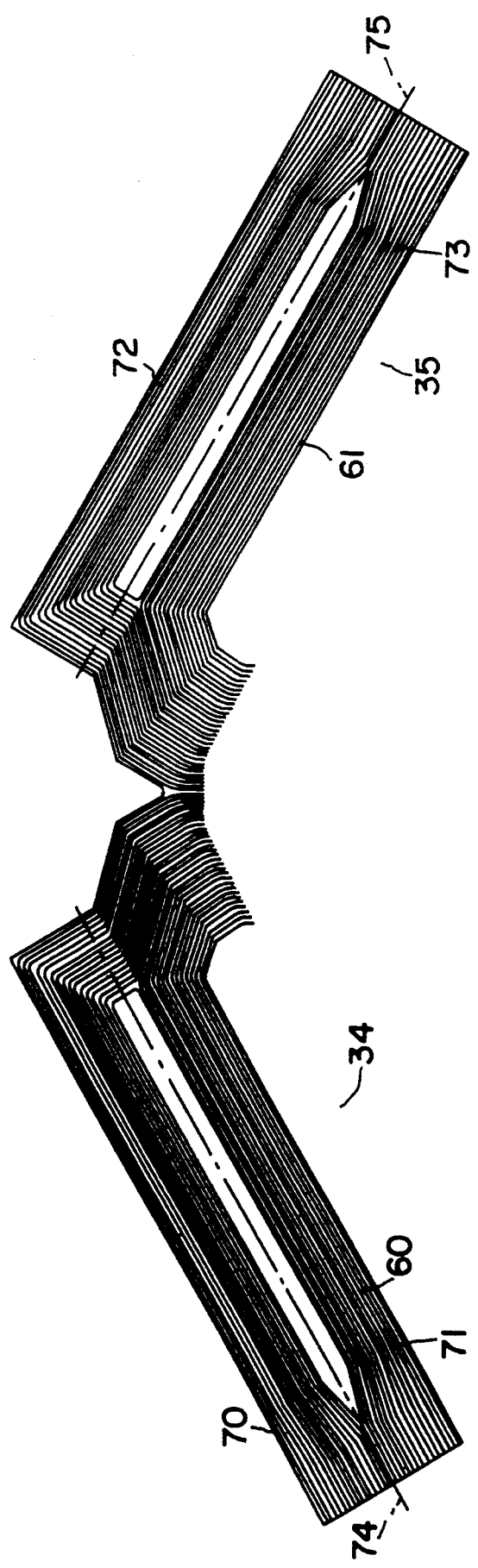
FIG. 6 shows a modification of the printed circuit board of FIG. 5.

An example of a flat blank of a flexible printed circuit board suitable for the purpose is shown in FIG. 6. The conductor tracks extending in the longitudinal direction of the elongated parts 60, 61 of the wing strips 34, 35 of the flexible printed circuit board have in each case been divided into two groups 70, 71 and 72, 73 respectively, each lying on one side of the folding lines 74 and 75 respectively. Thereby the height necessary for the flexible printed circuit board is reduced considerably.

When a flexible printed circuit board is applied having folded elongated parts of the wing strips and when more than connecting elements are applied between the flexible printed circuit board and the cables 30, ..., 33 printed circuit boards 43, 44 the printed circuit boards 43, 44 can be provided with conductor tracks on both sides, and each side of each printed circuit board 43 or 44 then corresponds to one of the parts 70, ..., 73.

In principle, two (or more) individual flexible printed circuit boards could also be used. The use of a single printed circuit board gives the advantage that the position of the tracks, in particular in the end strips, is determined accurately. With the correct selection of the centre-to-centre distance of the tracks, these can also be placed accurately in line with the gold electrodes of the transducer elements and, after correct positioning of a printed circuit board, a shifting of any second printed circuit board cannot take place.

The transducer housing 14 in the example shown is mounted in the aperture 9 of the holder 8 by a simple O-ring 46, which also forms a seal. It is also possible to use a bearing sleeve or another suitable bearing structure.

It is pointed out that, after the above, various modifications are obvious for the expert. For example, a cap can be placed over the lens to cover the gap between the transducer housing and the edge of the aperture 9. An acoustic coupling fluid must then be applied under such a cap.

The belt 17 could also be replaced by another transmission mechanism such as a toothed rack which can be shifted by a pulling cable in the lengthwise direction, and which engages on a toothed wheel directly or indirectly coupled to the transducer housing. In that case it could be possible to make do with one pulling cable. Springs which press the transducer housing back to a predetermined rest position could also be used.

Instead of a single, folded or unfolded flexible printed circuit board, two or more flexible printed circuit boards or one or more bunches of wires connected between the connectors 40, 41 and to the cables 30 to 33 could be used, as already stated.

The belt 17 can also be made narrower and preferably lies slightly recessed in a groove in the transducer housing.

The transducer, which in the example shown is essentially flat and hexagonal, can also be, for example, round or rectangular and slightly concave or even convex, It is also pointed out that the probe described can also in principle be used for examination through body cavities other than the oesophagus.

These and similar modifications are considered to fall within the scope of the invention.

I claim:

1. An endoscopic probe, which comprises: a probe head including a cylindrically-shaped transducer housing rotatably disposed therein;
   an ultrasonic transducer of the phase array type formed of a plurality of elongated transducer elements disposed within said transducer housing, said ultrasonic transducer having a longitudinal axis perpendicular to a longitudinal axis of said probe head;
   means for rotating said ultrasonic transducer in said transducer housing within a plane of said phase array of said ultrasonic transducer;
   a loop-shaped flexible circuit board extending into said ultrasonic housing and connected to said plurality of elongated transducer elements;
   a flexible tube connected to said probe head; and
   conductors extending through said flexible tube electrically connected to said flexible circuit board.

2. The endoscopic probe as defined in claim 1 wherein an opening in said transducer housing extends over a circular arc of about 180°.

3. The endoscopic probe as defined in claims 1 or 2 and further including a pin member fitted in said transducer housing for guiding therearound said flexible printed circuit board.

4. The endoscopic probe as defined in claim 3 and further including two pin members fitted in said transducer housing and extending substantially parallel to said longitudinal axis of said transducer housing on either side of said longitudinal axis of said probe head wherein said flexible printed circuit board is guided between said pin members.

5. The endoscopic probe as defined in claim 1 wherein said transducer housing includes a backing layer disposed in an electrically insulating frame member in which is positioned said ultrasonic transducer.

6. The endoscopic probe as defined in claim 5 wherein said flexible printed circuit board is disposed beneath said backing layer of said transducer housing.

7. The endoscopic probe as defined in claim 1 and further including a support plate, proximate said probe head and a printed circuit board positioned on said support plate whereby conductor tracks on said printed circuit board are in electrical contacting relationship with conductor tracks of said flexible printed circuit board.

8. The endoscopic probe as defined in claim 1 wherein said flexible printed circuit board in an unfolded state is substantially V-shaped forming two wing strips, each wing strip comprising an elongated part and a short transverse part having an end part of conductors connected to separate elongated transducer elements.

9. The endoscopic probe as defined in claim 8 wherein each elongated part of each wing strip is comprised of two conductor tracks on either side of a fold line extending in a longitudinal direction of said wing strip.

10. The endoscopic probe as defined in claim 1 wherein said means for rotating said ultrasonic transducer comprise a belt member coursed about said ultrasonic transducer housing and having free ends connected to pull cables extending through said flexible tube.

11. The endoscopic probe as defined in claim 10 wherein said belt member comprises spring steel.

12. The endoscopic probe as defined in claim 10 and further including a metal strip-like member rigidly connected to said ultrasonic transducer housing and connected to said belt member by a spot weld.

* * * * *